(12) United States Patent
Lin et al.

(10) Patent No.: US 10,045,839 B2
(45) Date of Patent: Aug. 14, 2018

(54) METHODS FOR FABRICATING DENTAL PROSTHESES

(71) Applicant: University of Louisville Research Foundation, Inc., Louisville, KY (US)

(72) Inventors: Wei-Shao Lin, Louisville, KY (US); Amirali Zandinejad, Louisville, KY (US); Dean Morton, Louisville, KY (US)

(73) Assignee: UNIVERSITY OF LOUISVILLE RESEARCH FOUNDATION, INC., Louisville, KY (US)

( * ) Notice: Subject to any disclaimer, the term of this patent is extended or adjusted under 35 U.S.C. 154(b) by 654 days.

(21) Appl. No.: 14/421,188

(22) PCT Filed: Aug. 13, 2013

(86) PCT No.: PCT/US2013/054751
§ 371 (c)(1),
(2) Date: Feb. 12, 2015

(87) PCT Pub. No.: WO2014/028505
PCT Pub. Date: Feb. 20, 2014

(65) Prior Publication Data
US 2015/0320525 A1 Nov. 12, 2015

Related U.S. Application Data

(60) Provisional application No. 61/682,747, filed on Aug. 13, 2012.

(51) Int. Cl.
*A61C 13/00* (2006.01)
*B22F 3/105* (2006.01)
(Continued)

(52) U.S. Cl.
CPC ........ *A61C 13/0018* (2013.01); *A61C 8/0012* (2013.01); *A61C 13/0019* (2013.01);
(Continued)

(58) Field of Classification Search
CPC ........ B22F 3/1055; B33Y 10/00; B33Y 80/00
See application file for complete search history.

(56) References Cited

U.S. PATENT DOCUMENTS 5,839,900 A * 11/1998 Billet ................. A61C 13/0003
433/202.1
6,271,282 B1 * 8/2001 Giordano ........... A61C 13/0003
523/115
(Continued)

FOREIGN PATENT DOCUMENTS

EP 1354567 B1 10/2003
WO 2012064620 A1 5/2012

OTHER PUBLICATIONS

Kuroda D., Niinomi M., Morinaga M., Kato Y., Yashiro T. Design and mechanical properties of new b type titanium alloys for implant materials. Mater Sci Eng A 1998; 243: 244-9.
(Continued)

*Primary Examiner* — Scott R Kastler
*Assistant Examiner* — Vanessa T. Luk
(74) *Attorney, Agent, or Firm* — Stites & Harbison, PLLC; Terry L. Wright (57) ABSTRACT

Methods of fabricating dental prostheses are provided that include the steps of providing a powder of a dental material, and then selectively melting the powder of the dental material to produce a functionally graded layer of the dental material. Additional layers of functionally graded dental material are then built on top of the initial layer of dental material to thereby produce a three-dimensional dental prosthesis having a functionally graded structure and a desired
(Continued)

physical geometry. Dental prostheses produced by the foregoing methods are also provided.

6 Claims, 6 Drawing Sheets

(51) Int. Cl.
| | |
|---|---|
| B33Y 10/00 | (2015.01) |
| C22C 14/00 | (2006.01) |
| A61K 6/04 | (2006.01) |
| A61C 8/00 | (2006.01) |
| B33Y 50/00 | (2015.01) |
| B33Y 80/00 | (2015.01) |

(52) U.S. Cl.
CPC .............. *A61K 6/04* (2013.01); *B22F 3/1055* (2013.01); *C22C 14/00* (2013.01); *B22F 2207/00* (2013.01); *B33Y 10/00* (2014.12); *B33Y 50/00* (2014.12); *B33Y 80/00* (2014.12)

(56) References Cited

U.S. PATENT DOCUMENTS

| | | | |
|---|---|---|---|
| 7,666,522 B2 | 2/2010 | Justin et al. | |
| 7,951,412 B2 | 5/2011 | Justin et al. | |
| 8,491,936 B2 | 6/2013 | Rabiei et al. | |
| 2007/0203584 A1* | 8/2007 | Bandyopadhyay | A61F 2/28 623/23.5 |
| 2008/0206710 A1 | 8/2008 | Kruth et al. | |
| 2008/0213727 A1 | 9/2008 | Zhang et al. | |
| 2010/0143868 A1 | 6/2010 | Hintersehr | |
| 2010/0291401 A1* | 11/2010 | Medina | B23K 15/0086 428/593 |
| 2012/0148983 A1 | 6/2012 | Mullen et al. | |

OTHER PUBLICATIONS

Niinomi M. Biologically and Mechanically Biocompatible Titanium Alloys. Materials Transactions 2008; 49 (10) 2170-2178.
Guillemot F. Recent advances in the design of titanium alloys for orthopedic applications. Expert Rev Med Devices. 2005; 2: 741-8.
Parr G. Titanium: the mystery metal of implant dentistry. J Prosthet Dent 1985; 54: 410-3.
Bhattarai S.R., Khalil K.A., Dewidar M., Hwang P.H., Yi H.K., Kim H.Y. Novel production method and in-vitro cell compatibility of porous Ti-6Al-4V alloy disk for hard tissue engineering. J Biomed Mater Res A. 2008; 86: 289-99.
Krishna B.V., Bose S., Bandyopadhyay A. Low stiffness porous Ti structures for load-bearing implants. Acta Biomater. 2007; 3: 997-1006.
Turner T.M., Sumner D.R., Urban R.M., Rivero D.P., Galante J.O. A comparative study of porous coatings in a weight-bearing total hip-arthroplasty model. J Bone Joint Surg Am 1986; 68: 1396-409.
Head W.C., Bauk D.J., Emerson Jr R.H. Titanium as the material of choice for cementless femoral components in total hip arthroplasty. Clin Orthop Relat Res 1995; 311: 85-90.
Oh I.H., Nomura N., Masahashi N., Hanada S. Mechanical properties of porous titanium compacts prepared by powder sintering. Scripta Mater. 2003; 49: 1197-202.
Hollander D.A., Von Walter M., Wirtz T., Sellei R. Structural, mechanical and in vitro characterization of individually structured Ti-6Al-4V produced by direct laser forming. Biomaterials. 2006; 27: 955-63.
Stamp R., Fox P., O'Neill W., Jones E., Sutcliffe C. The development of a scanning strategy for the manufacture of porous biomaterials by selective laser melting. J Mater Sci Mater Med. 2009; 20: 1839-48.
Traini T., Mangano C., Sammons R.L., Mangano F. Direct laser metal sintering as a new approach to fabrication of an isoelastic functionally graded material for manufacture of porous titanium dental implants. Dent Mater. 2008; 24: 1525-33.
Mullen L., Stamp R.C., Brooks W.K., Jones E., Sutcliffe C.J. Selective Laser Melting: a regular unit cell approach for the manufacture of porous, titanium, bone in-growth constructs, suitable for orthopedic applications. J Biomed Mater Res B Appl Biomater. 2009; 89: 325-34.
Santos E.C., Shiomi M., Osakada K., Laoui T. Rapid manufacturing of metal components by laser forming. Int J Mach Tools Manuf 2006; 46: 1459-1468.
Tolochko N.K., Laoui T., Khlopkov Y.V., Mozzharov S.E., Titov V.I., Ignatiev M.B. Absorptance of powder materials suitable for laser sintering. Rapid Prototyping J 2000; 6: 155-160.
Bandyopadhyay A., Espana F., Balla V.K., Bose S. Influence of porosity on mechanical properties and in vivo response of Ti6Al4V implants. Acta Biomater. 2010; 6: 1640-8.
Pilliar R.M. Porous-surfaced metallic implants for orthopaedic applications. J Biomed Mater Res—Appl Biomater 1987; 21: 1-33.
Clemow A.J.T., Weinstein A.M., Klawitter J.J., Koeneman J., Anderson J. Interface mechanics of porous titanium implants. J Biomed Mater Res 1981; 15: 73-82.
Wennerberg A., Albrektsson T. Effects of titanium surface topography on bone integration: a systematic review. Clin Oral Implants Res. 2009; 20: 172-84.
Shalabi M.M., Gortemaker A., Van'T Hof M.A., Jansen J.A., Creugers N.H. Implant surface roughness and bone healing: a systematic review. J Dent Res. 2006; 85: 496-500.
Le Guéhennec L., Soueidan A., Layrolle P., Amouriq Y. Surface treatments of titanium dental implants for rapid osseointegration. Dent Mater. 2007; 23: 844-54.
Hodosh M., Povar M., Shklar G. The dental polymer implant concept. J Prosthet Dent 1969: 22: 371-380.
Pirker W., Kocher A. Immediate, non-submerged, root-analogue zirconia implant in single tooth replacement. Int J Oral Maxillofac Surg. 2008; 37: 293-5.
Kohal R.J., Hürzeler M.B., Mota L.F., Klaus G., Caffesse R.G., Strub J.R. Custom-made root analogue titanium implants placed into extraction sockets. Clin Oral Implants Res 1997; 8: 386-392.
Pirker W., Kocher A. Immediate, non-submerged, root-analogue zirconia implants placed into single-rooted extraction sockets: 2-year follow-up of a clinical study. Int J Oral Maxillofac Surg. 2009; 38: 1127-32.
Zhang Y., Chai H., Lawn B.R. Graded Structures for All-ceramic restorations. J Dent Res. 2010; 89(4): 417-421.
Zhang Y., Chai H., Lawn B.R. Chipping resistance of graded zirconia ceramics for dental crowns. J Dent Res. 2012; 91(3): 311-315.
Baggi L., Cappelloni I., Di Girolamo M., Maceri F., Vairo G. The influence of implant diameter and length on stress distribution of osseointegrated implants related to crestal bone geometry: a three-dimensional finite element analysis. J Prosthet Dent. 2008;100:422-31.
Lee J.S., Cho I.H., Kim Y.S., Heo S.J., Kwon H.B., Lim Y.J. Bone-implant interface with simulated insertion stress around an immediately loaded dental implant in the anterior maxilla: a three-dimensional finite element analysis. Int J Oral Maxillofac Implants. 2012;27:295-302.
Van Noort R. The Future of Dental Devices is Digital. Dental Materials. 2012; 28:3-12.
Atzeni E., Iuliano L., Minetola P., Salmi A. Proposal of an Innovative Benchmark for Accuracy Evaluation of Dental Crown Manufacturing. Computers in Biology and Medicine. 2012; 42:548-555.
Silva N.F.R.A., Witek L., Coelho P.G., Thompson V.P., Rekow E.D., Smay J. Additive CAD/CAM Process for Dental Prostheses. Journal of Prosthodontics. 2011; 20:93-96.
Ebert J., Ozkol E., Zeichner A., Uibel K., Weiss O., Koops U., Telle R., Fischer H. Direct Inkjet Printing of Dental Prostheses Made of Zirconia. Journal of Dental Research. 2009; 88(7):673-676.
Conrad H.J., Seong W.J., Pesun I.J. Current ceramic materials and systems with clinical recommendations. J Prosthet Dent, 2007; 98:389-404.
Denry I., Holloway J.A. Ceramics for Dental Applications: A Review. Materials. 3(2010): 351-368.

(56) References Cited

OTHER PUBLICATIONS

Rizkalla AS, Jones DW. Mechanical properties of commercial high strength ceramic core materials. Dent Mater. 2004;20:207-12.

Rizkalla AS, Jones DW. Indentation fracture toughness and dynamic elastic moduli for commercial feldspathic dental porcelain materials. Dent Mater. 2004;20:198-206.

Guess P.C., Schultheis S., Bonfante E.A., Coelho P.G., Ferencz J.L., Silva N.R.F.A. All-Ceramic Systems: Laboratory and Clinical Performance. Dental Clinics of North America. 55(2011): 333-352.

Heintze S.D., Rousson V. Survival of Zirconia- and Metal-supported Fixed Dental Prostheses: A Systematic Review. Introductory Journal of Prosthodontics. 6(2010): 493-502.

Raigrodskia. J., Hillstead M.B., Meng G.K., Chung K.H. Survival and Complications of Zirconia-based Fixed Dental Prostheses: A Systematic Review. Journal of Prosthetic Dentistry. 107(2012): 170-177.

Sailer I., Fehér A., Filser F., Gauckler L.J, Luthy H., Hammerle C.H. Five-year clinical results of zirconia frameworks for posterior fixed partial dentures. Introductory Journal of Prosthodontics. 20(2007): 383-388.

Schwarz S., Shroder C., Hassel A., Bomicke W., Rammelsberg P. Survival and Chipping of Zirconia-based and Metal-ceramic Implant-supported Single Crowns. Clinical Implant Dentistry and Related Research. 14(2011): 119-125.

He L., Swain M.W. Enamel—A Functionally graded natural coating. Journal of Dentistry. 37(2009): 596-603.

An B., Wang R., Arola D., Zhang D. The role of property gradients on the mechanical behavior of human enamel. Journal of the Mechanical Behavior of Biomedical Materials. 9(2012): 63-72.

Zhang Y., Kim J. Graded structure for damage resistant and aesthetic all-ceramic restorations. Dental Materials. 25(2009): 781-790.61.

Zhang Y., Ma L. Optimization of ceramic strength using elastic gradients. Acta Materialia. 57(2009): 2721-2729.

Zhang Y. Overview: Damage resistance of graded ceramic restorative materials. Journal of the European Ceramic Society. 32(2012): 2623-2632.

Zhang Y., Sun M-J, Zhang D. Designing functionally graded materials with superior load-bearing properties. Acta Biomaterialia. 8(2012): 1101-1108.

Katz R.N. Advanced ceramic (Dental ceramic). Nov. 21, 2000.

Harlan N., Park, S-M., Bourell D.L., Beaman J.J.. Selective laser sintering of zirconia with micro-scale features. Proceedings of the 10th Solid Freeform Fabrication Symposium, Austin, TX, USA, 1999.

Wang H., Bourell D.L., Beaman J.J. Selective laser sintering of quartz powder. Proceedings of the 8th Solid Freeform Fabrication Symposium, Austin, TX, USA, 1997.

Klocke F., Wirtz, H.. Selective laser sintering of zirconium silicate. Proceedings of the 9th Solid Freeform Fabrication Symposium, Austin, TX, USA, 1998.

Denham H.B., Cesarano J., King B.H. Mechanical behavior of robocast alumina. Proceedings of the 9th Solid Freeform Fabrication Symposium, Austin, TX, USA, 1998.

Dai C., Qi G., Rangarajan S., Wu S., Langrana N.A., Safari A., Danforth S. C. High quality, fully dense ceramic components manufactured using fused deposition of ceramics (FDC). Proceedings of the 8th Solid Freeform Fabrication Symposium, Austin, TX, USA, 1997.

Levy R.A., Chu T-M.G., Halloran J.W., Feinberg S.E., Hollister S. CT-generated porous hydroxyapatite orbital floor prosthesis as a prototype bioimplant. American Journal of Neuroradiology. 18(1997): 1522-1525.

Cima M.J., Oliveira M., Wang H.R., Sachs E., Holman R. Slurry-based 3DP and fine ceramic components. Proceedings of the 12th Solid Freeform Fabrication Symposium, Austin, TX, USA, 2001.

Uhland S, Holman R, Debear B, Saxton P, Cima M, Sachs E. Three-dimensional printing, 3DP, of electronic ceramic components. Proceedings of the 10th Solid Freeform Fabrication Symposium, Austin, TX, USA, 1999.

Yang L., Zhang S., Oliveira G., Stucker B. Development of a 3D printing method for production of dental application. Proceedings of the 24th Solid Freeform Fabrication Symposium, Austin, TX, USA, 2013.

Jackson T.R., Liu H., Patrikalakis N.M., Sachs E.M., Cima M.J. Modeling and designing functionally graded material components for fabrication with local composition control. Materials and Design. 20(1999): 63-75.

Noecker F.F., Dupont J.N. Functionally Graded Copper—Steel Using Laser Engineered Net Shaping Process. Proceedings of the 13th Solid Freeform Fabrication Symposium, Austin, TX, USA, 2002.

Gasdaska C., Clancy R., Ortiz M., Jamalabad V., Virkar A., Popovitch D. Functionally Optimized Ceramic Structures. Proceedings of the 9th Solid Freeform Fabrication Symposium, Austin, TX, USA, 1998.

Jafari M.A., Han W., Mohammadi F., Safari A., Danforth S.C., Langrana N. A novel system for fused deposition of advanced multiple ceramics. Rapid Prototyping Journal. 692000): 161-174, vol. 6 (2000).

He L., Yin Z., Van Vuuren L.J., Carter E.A., Liang, X. A natural functionally graded biocomposite coating-human enamel. Acta Biomaterialia. 9(5), 2013: 6330-6337.

Jones D.W., "Development of dental ceramics: an historical prospective", Dent Clin N 29: 621-644, (Oct. 1985).

Barreiro M.M, Riesgo O., Vicente E. E, "Phase identification in dental porcelains for ceramo-metallic restorations", Dent Mater 5:51-7, (Jan. 1989).

Burke F.J., Lucarotti P.S., "Ten-year outcome of crowns placed with in the General Dental Services in England and Wales", J Dent 37:12-24, (2009).

Rekow E.D., Silva N.R.F.A., Coelho P.G., Zhang Y., Guess P., Thompson V.P., "Performance of dental ceramics: challenges for improvements", J Dent Res 90:937-952, (2011).

Pjetursson B.E., Sailer I., Zwahlen M., Hammerle C.H., "A systemic review of the survival and complication rates of all-ceramic and metal-ceramic reconstructions", J Dent Reg 90:938-986, (2007).

Valenti M., Valenti A, "Retrospective survival analysis of 261 lithium disilicate crowns in a private general practice", Quintessence Int 40: 573-579, (Jul./Aug. 2009).

Whittneben J.G., Write R.F., Weber H.P., Gallucci G.O., "A systematic review of the clinical performance of CAD/CAM single-tooth restorations", Int J Prosthodont 22:466-471, (2009).

Zhang S., Yang L., Zandinejad A., Miyanaji H., Stucker B., An experimental study of ceramic dental porcelain materials using a 3D print (3DP) process. Proceeding of Solid Freeform Fabrication (SFF) Symposium, 2014.

Gonzaga C.C., Yoshimura H.N., Cesar P.F., Miranda Jr W.G., "Subcritical crack growth in porcelains, glass-ceramics, and glass-infiltrated alumina composite for dental restorations", J Mater Sci Mater Med 20: 1017-24,(2009).

Fairhurst C.W., Lockwood P.E., Ringle R.D., Twiggs S.W.' "Dynamic fatigue of feldspathic porcelain", Dent Mater 9: 269-73, (Jul. 1993).

Yoshimura H.N., Cesar P.F., Miranda W.G., Gonzaga C.C., Okada C.Y., Goldenstein H., "Fracture toughness of dental porcelains evaluated by IF, SCF, and SEPB methods", Am Ceram Soc 88: 1680-3, (2005).

Li J., Liao H., Hermansson L. Sintering of partially-stabilized zirconia and partially-stabilized zirconia—hydroxyapatite composites by hot isostatic pressing and pressureless sintering, Biomaterials, 17 (1996), 1787-1790.

Itoh H., Wakisaka Y., Ohnuma Y., Kuboki Y. A new porous hydroxyapatite ceramic prepared by cold isostatic pressing and sintering synthesized flaky powder. Dental Materials Journal, 13 (1994), 25-35.

Denry I. and Kelly R., State of the art of zirconia for dental applications. Dental Materials, 24 (2008), 299-307.

Martorelli M., Gerbino S., Giudice M., Ausiello P. A comparison between customized clear and removable orthodontic appliances manufactured using RP and CNC techniques, 29 (2013), e1-e10.

(56) References Cited

OTHER PUBLICATIONS

Mohanty S., Rameshbabu A.P., Dhara S., Net shape forming of green alumina via CNC machining using diamond embedded tool. 39 (2013), 8985-8993.

Wu M., Tinschert J., Augthun M., Wagner I., Schädlich-Stubenrauch J., Sahm P.R., Spiekermann H. Application of laser measuring, numerical simulation and rapid prototyping to titanium dental castings. Dental Materials, 17 (2001), 102-108.

Azari a., Nikzad S., The evolution of rapid prototyping in dentistry: a review. Rapid Prototyping Journal, 15 (2009), 216-225.

Wang J., Shaw L., Cameron T. Solid Freeform Fabrication of permanent dental restorations via slurry micro-extrusion. Journal of the American Ceramic Society, 89 (2006), 346-349.

Khalyfa A., Vogt S., Weisser J., Grimm G., Rechtenbach A., Meyer W., Schnabelrauch M. Development of a new calcium phosphate powder-binder system for the 3D printing of patient specific implants. 18 (2007), 909-916.

Lam C.X.F., Moa X.M, Teoha S.H., Hutmacher D.W. Scaffold development using 3D printing with a starch-based polymer. 20 (2002), 49-56.

Scientific documentation IPS InLine system, 2010.

Aerosil R 972 Hydrophobic fumed silica MSDS, (print date: Aug. 7, 2015).

Spierings A.B., Schneider M. Comparison of density measurement techniques for additive manufactured metallic parts. Rapid Prototyping Journal, 17(5), 2011, 380-386.

Giannakopoulos AE, et al. Development of strong surfaces using functionally graded composites inspired by natural teeth. Journal of engineering materials and technology, 2010 132(1).

\* cited by examiner

METHODS FOR FABRICATING DENTAL PROSTHESES

RELATED APPLICATIONS

This application claims priority from U.S. Provisional Application Ser. No. 61/682,747, filed Aug. 13, 2012, the entire disclosure of which is incorporated herein by this reference.

TECHNICAL FIELD

The present invention relates to methods for fabricating dental prostheses. In particular, the present invention relates to methods for fabricating dental prostheses whereby a powder of a dental material is selectively melted to produce a three-dimensional dental prosthesis having a desired physical geometry and one or more functionally graded mechanical properties.

BACKGROUND

Titanium and its alloys have been utilized as desirable materials for dental and orthopedic prostheses because of their excellent corrosion resistance, biocompatibility, mechanical properties, and high strength-to-weight ratio. [1-4] However, one major concern regarding the use of these titanium prostheses in medical or dental applications is the mismatch of the Young's modulus between the bone (10-30 GPa) and the titanium material (110 GPa). [5,6] Because of that mismatch, bone is often insufficiently loaded and becomes stress-shielded, which then leads to higher bone resorption. Indeed, this mismatch of the Young's moduli has been identified as a factor for the loosening of dental implants that occurs following stress shielding of bone and may result in detrimental resorptive bone remodeling. [7-8]

Recently, the introduction of an amount of porosity into titanium and its alloys, both of which are typically used to produce at least a portion of current dental prostheses, has been proposed to reduce the Young's modulus of titanium and potentially overcome the foregoing detrimental effects. [9] To date, however, the introduction of a sufficient degree of porosity into titanium-based prostheses has yet to be completely achieved, both from a customization standpoint and from an economical standpoint. Modern dental prostheses, such as dental implants, are predominantly produced by the machining of solid titanium rods, followed by applying different surface treatments and geometries to improve stability and enhance osseointegration of the prostheses. However, none of the conventional techniques are capable of producing a controlled porosity, much less a completely controlled geometry and external surface morphology in a limited number of steps. [10-13]

Researchers have also proposed the placement of custom-made root-analogue implants into an extraction socket to reduce bone and soft-tissue trauma. [24] In those initial clinical studies, root-identical titanium implants demonstrated favorable results with 100% primary stability at insertion and 1-month follow up; however, an extremely high failure rate of 48% was then found over a short time period of 9-months post-operation. [25-27] In a more recent clinical trial, immediate, non-submerged, custom-made root-analogue zirconia implants (with surface macro-retentive feature and reduced implant diameter at the cortical bone area) placed into single-rooted extraction sockets showed an overall survival rate of 92% as late as 33 months under functions. [28] Satisfactory esthetic and functional results were also achieved with the composite crowns in those studies, with minimal soft and hard peri-implant tissue resorption being observed, but the ability to produce custom-made prostheses with a user-defined complexity was nonetheless still limited.

Similar to the issues encounter in fabricating implants, ceramic materials have been used for decades to improve esthetic outcomes (i.e., the appearance) of dental restorations. In fabricating such dental restorations, the intent has been to closely imitate the optical properties of natural teeth, while maintaining acceptable biomechanical characteristics and biocompatibility. With the several ceramic materials (glass and oxide ceramics) and methods for fabrication (conventional, press and Cad-Cam) that are currently employed, however, each of the currently-available ceramic dental restorations exhibit a number of shortcomings, including a higher incidence of fracture compared to prostheses fabricated exclusively out of dental alloys.

Accordingly, a method of fabricating a dental prosthesis, such as a dental implant or dental restoration, that allows greater control over the mechanical properties of the dental prosthesis, but that is also capable of producing a custom-made prosthesis having a desired physical geometry and external surface morphology in an efficient and economical manner would be both highly-desirable and beneficial.

SUMMARY

The present invention meets some or all of the above-identified needs, as will become evident to those of ordinary skill in the art after a study of information provided in this document.

This summary describes several embodiments of the present invention, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the present invention, whether listed in this summary or not. To avoid excessive repetition, this summary does not list or suggest all possible combinations of such features.

The present invention includes methods for fabricating dental prostheses. In some implementations of the presently-disclosed methods, a powder of a dental material is first provided. The powder of the dental material is then selectively melted to produce a functionally graded layer of dental material. Subsequent to the production of the initial functionally graded layer of the dental material, additional dental material powder is placed on that initial layer and is selectively melted to produce a second layer of dental material atop the initial layer. Such a spreading and selectively melting of additional powders of dental material is then repeated until a three-dimensional dental prosthesis is produced having a functionally graded structure and desired geometry.

In certain implementations of the presently-disclosed methods of producing a functionally graded, three-dimensional dental prosthesis, selectively melting the powder of dental material includes fully melting a first portion (e.g., an outer portion) of the powder of dental material and partially melting a second portion (e.g., a core portion) of the powder of dental material to produce a layer of dental material having a first area with a density greater than that of a second area. In some embodiments, selectively melting the powder of the dental material comprises varying an amount of heat energy applied to the powder of dental material to produce a layer having a portion with a density, porosity, or both different than that of an adjacent portion in the layer. In some implementations, selectively melting the powder of the dental material comprises selective laser melting of the powder of the dental material.

With respect to the dental materials used in accordance with the presently-disclosed methods, dental materials capable of being implanted into a subject and capable of undergoing selective melting to produce a functionally graded structure are preferably used. In some implementations, the dental material is selected from the group consisting of a metal, a metal alloy, a ceramic, a resin material, or combinations thereof. For example, in some implementations, the dental material is either lithium disilicate, leucite, mica, titanium, titanium alloy, gold, gold alloy, zirconium oxide, or combinations thereof. In one implementation, the dental material is a titanium alloy having about 6 wt % aluminum and about 4 wt % vanadium.

With further respect to the fabrication of a dental prosthesis in accordance with the presently-disclosed methods, in some implementations, the three-dimensional dental prosthesis that is produced is a dental implant. In some implementations, the implant is produced by melting a first portion of a dental powder by applying a laser having a power of about 170 W to the powder, and then selectively meting a second portion of the powder of dental material by applying a laser having a power of about 43 W to the powder. In some implementations, the portion of the dental power exposed to the higher power laser can comprise an upper portion of the dental implant, while the portion of the dental powder exposed to the lower power laser can comprise the lower portion of the dental implant. In some implementations, the dental implant produced by the foregoing methods has a strength of about 300 MPa or an elastic modulus of about 30 GPa.

In yet further implementations of the presently-disclosed methods, the three-dimensional dental prosthesis that is fabricated comprises a dental restoration. In some implementations, through the selective melting of a dental powder, a first portion of powder of a dental material can be melted to produce an outer portion of the dental restoration having a greater density than a core portion of the dental restoration, which is produced by melting a second portion of the powder of the dental material. In some implementations, an outer portion of a dental restoration is produced that has an elastic modulus of about 60 GPa to about 120 GPa, a hardness of about 1 GPa to about 4 GPa, or a flexural strength of about 0.6 GPa to about 1.0 GPa. In some implementations, a core portion of a dental restoration is produced that has an elastic modulus of about 15 GPa to about 30 GPa, a hardness of about 0.6 GPa to about 1.0 GPa, or a flexural strength of about 0.2 GPa to about 0.6 GPa.

In a further implementation of the presently-disclosed methods, the dental restoration that is produced is a full contour crown that includes an outer enamel-like portion having an outer layer and an inner layer, and an inner dentin-like portion. In such implementations, the outer enamel-like portion of the crown has a width that extends from the outer layer to the inner layer, where the hardness and the elastic modulus of the enamel-like portion reduces gradually across the width of the enamel-like portion from the outer layer to the inner layer. In some implementations, the outer layer of such an enamel-like portion has an elastic modulus of about 100 GPa to about 140 GPa and a hardness of about 0.8 GPa to about 1.2 GPa, and the inner layer of such an enamel like-portion has an elastic modulus of about 40 GPa to about 60 GPa and a hardness of about 0.4 GPa to about 0.8 GPa. In some implementations, the dentin-like portion of such a crown has an elastic modulus of about 15 GPa to about 45 GPa.

Still further provided, in some implementations of the presently-disclosed methods, are methods of fabricating a dental prosthesis whereby a dental prosthesis is produced and is configured to correspond to the dental or anatomical structures of a subject. In some implementations, a method of fabricating a dental prosthesis is provided where information relating to a dental or anatomical structure of a subject is first received. A powder of a dental material is then provided as described above. However, rather than selectively melting the powder of dental material in a standard or predetermined format, the powder of dental material is selectively melted based on received dental or anatomical structure information specific to a particular subject in order to produce a functionally graded layer of the dental material. Repeated layers can then be fabricated based on the provided information to thereby produce a three-dimensional dental prosthesis that has a functionally graded structure and that is particularly configured to the dental and anatomical information (e.g., dental and anatomical structures or a lack thereof) for a particular subject.

Further features and advantages of the present invention will become evident to those of ordinary skill in the art after a study of the description, figures, and non-limiting examples in this document.

DESCRIPTION OF EXEMPLARY EMBODIMENTS

The details of one or more embodiments of the present invention are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by one of ordinary skill in the art, definitions are set forth herein to facilitate explanation of the present invention.

Unless defined otherwise, all technical and scientific terms used herein have the same meaning as commonly understood by one of ordinary skill in the art to which the present invention belongs. Although any methods, devices, and materials similar or equivalent to those described herein can be used in the practice or testing of the present invention, representative methods, devices, and materials are now described.

Following long-standing patent law convention, the terms "a", "an", and "the" refer to "one or more" when used in this application, including the claims. Thus, for example, reference to "an implant" includes a plurality of such implants, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the present invention.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The present invention relates to methods of fabricating dental prostheses and, more particularly, methods of fabricating dental prostheses whereby a powder of a dental material is selectively melted to produce a three-dimensional dental prosthesis having a desired physical geometry and one or more functionally graded mechanical properties. In some embodiments, the methods of the present invention advantageously allow the physical geometry of the dental prosthesis, such as the surface geometry, the width, length, and shape of the prosthesis, and the surface roughness of the prosthesis, to be customized so as to provide a dental prosthesis with a physical geometry identical or similar to those found in a naturally-occurring tooth.

It is appreciated that rapid prototyping (RP), also known as solid freeform fabrication, is a fabrication process capable of directly generating physical objects with a defined structure and shape from virtual-3D model data. [10] Selective laser sintering (SLS), selective laser melting (SLM), stereolithography (SL), blown powder cladding (BPC) and three-dimensional printing (3DP) are all among the commonly implemented processing techniques for rapid prototyping techniques. In each of these processes, three-dimensional virtual data representing the object's physical geometry is first sliced into thin horizontal layers using a mathematical algorithm. Then, the data representing each horizontal layer is used to deposit material in a layer-wise structure based on the three-dimensional design. Finally, these steps are repeated, with each layer being connected to each other until the final physical geometry is completed. [11]

It has now been observed that rapid prototyping processes allow prostheses, such as dental implants, to be produced more economically than by traditional techniques. More specifically, it has been observed that a selective layer laser melting process, which makes use of different fabrication parameters to produce both fully melted (solid) and partially melted (more porous) structures from dental materials, can be used create dental and/or orthopedic prostheses having complex geometries and controlled gradient porosities that can not be produced using conventional machining techniques. As described in further detail below, it has been discovered that these fabricated prostheses have similar Young's moduli as that found in bone tissue, and are further able to reduce the mismatches of Young's moduli to provide a prosthesis capable of achieving long-term stability and osseointegration. Moreover, it has been discovered that a custom prosthesis can be fabricated based on three-dimensional virtual data obtained from a subject (i.e., from a cone beam computerized tomography (CT) scan) to thereby provide a prosthesis having an individualized, defined physical geometry, as well as functionally graded mechanical properties that are specific to a particular subject.

In some implementations of the present invention, a method of fabricating a dental prosthesis is provided. The term "prosthesis," and grammatical variations thereof, is used herein to refer to a device or structure that can be used externally or can be implanted into the body of a subject, and that substitutes for or supplements a missing or defective part of the body of the subject. In this regard, the term "dental prosthesis" is used herein to refer to a prosthesis that can be used in the oral cavity of a subject, either as an external or implanted prosthesis. Such dental prostheses include, but are not limited to: dental implants, such as implant fixtures and implant abutments; dental restorations, such as crowns over dental implants or natural teeth, or indirect partial restorations; and soft tissue replacements or devices capable of replacing hard and/or soft tissue. In some implementations, the dental prosthesis is a dental implant. In some implementations, the dental prosthesis is a dental restoration.

In one exemplary implementation of the present invention, a method of fabricating a dental prosthesis is provided where a powder of dental material is first provided and is then exposed to a power source to selectively melt the powder and produce a layer of dental material. Various methods of selectively melting a powder of dental material can be used in accordance with the presently-disclosed methods including, but not limited to, the selective melting that occurs with direct metal laser sintering (DMLS), electron beam melting (EBM) selective laser melting (SLM), selective heat sintering (SHS), selective laser sintering (SLS), and the like. In one preferred implementation, selective melting of the powder of the dental material comprises selective laser melting of the powder. However, regardless of the particular method used to selectively melt the dental material powder, by selectively melting the powder using focused heat sources, in some implementations, the amount of heat energy applied to portions of powder can be varied so as to produce layers of dental material in which a first portion of powder is fully melted to yield an area of the resulting layer that has a greater density (e.g., density similar to that of cast metal), while a second portion of the powder is partially melted to produce a layer of dental material that is less dense and more porous as a result of the partial melting together of the particles of the powder. For example, in some implementations, an amount of laser energy applied to the powder of dental material is varied so as to produce a portion with a density different than that of an adjacent portion on the same layer. In some implementations, and as described in further detail below, by using a laser melting process, a layer of dental material is produced wherein an outer, circumferential portion of the layer of dental material has a density that is greater than that of a core portion of the layer, as shown in FIGS. 6A-6C and 7A-7B.

With respect to the dental materials used in accordance with methods of the present invention, any dental material capable of being implanted into a subject and capable of undergoing selective melting can be used without departing from the spirit and scope of the subject matter described herein. Such dental materials include, but are not limited to, metals, metal alloys, ceramics, resin materials, or combinations thereof. In some implementations, the dental material is selected from titanium (including commercially pure titanium and titanium alloy), gold or gold alloy, zirconium oxide, lithium disilicate, leucite, and mica. In some implementations, fluoroapatite ($Ca_5(PO_4)_3F$; calcium fluorophosphates), a hard crystalline solid is used, as fluoroapatite is a known constituent of tooth enamel and can be provided in a form that is translucent, as well as in green, blue, brown, violet, or colorless forms. In some implementations, the dental material comprises a titanium alloy having about 6 wt % aluminum and about 4 wt % vanadium. Of course, various other weight percents of aluminum and vanadium, as well as various weight percentages of the other foregoing materials, can also be used and can be selected for a particular application as desired.

As would be recognized by those of ordinary skill in the art, in implementations that make use of a laser as the source of heat energy, the laser energy applied to a powder of a dental material in a particular application will depend on the laser power, scanning velocity, spacing between scan lines, the thickness of the powder layer, and the size of the powder particles being melted. In some implementations, the laser power is in the range of about 20 W to about 200 W, such as about 170 W or about 43 W or about 85 W; the scanning velocity is about 0 to about 7000 mm/s, such as about 1250 mm/s; the spacing between scan lines is about 0 mm to about 0.3 mm, such as about 0.1 mm; and the thickness of the powder layer used to produce the layer of dental implant material is about 0 mm to about 0.15 mm, such as about 0.03 mm. In some exemplary implementations, the powders of dental materials are comprised of a spherical particles having a diameter of about 0 micrometers to about 45 micrometers, such as a particle size of about 10 micrometers.

Regardless of the particular laser energy applied and the size of a powder used for a particular application, in the methods of the present invention, once the initial layer of dental material is produced with the desired mechanical properties (e.g., densities), additional layers of dental material are then built on top of the initial layer by repeatedly providing and spreading a powder of dental material over the existing layers, and then selectively melting those powder layers to produce additional layers of dental material. In this regard, in some implementations of the present invention, by repeatedly fabricating layers of dental materials upon existing layers of dental material, a three-dimensional dental prosthesis can be created that is functionally graded, either along the horizontal axis, the vertical axis, or both of the dental prosthesis to thereby provide a dental prosthesis having mechanical properties that mimic those found in the tooth or natural bone of a subject (e.g., a strength of about 200 MPa and an elastic modulus of about 3 to about 20 GPa).

The term "functionally graded," and grammatical variations thereof, is used herein to refer to materials in which there is gradual variation in the composition, structure, or both the composition and structure of the materials. In a functionally graded material, such variations occur gradually throughout a given volume of the materials and result in corresponding changes in the properties of the materials. By having variations in the properties of the materials over the specified gradient, the materials can thereby be tailored for specific functions and/or applications. For example, in some implementations of the present invention, by producing and using layers of functionally graded dental materials to fabricate a three-dimensional dental prosthesis, a dental prosthesis having a bio-inspired design can be produced that then allows the dental prosthesis to more closely mimic a naturally-occurring dental structure, while also achieving an increased biocompatibility and longevity in a subject as compared to a conventional dental prosthesis.

As one exemplary fabrication of a dental prosthesis having properties similar to that found in the tooth of a subject, in one implementation of the present invention, the dental prosthesis that is produced comprises an implant fixture or, in other words, an artificial root of a tooth. In that implementation, spherical particles of a titanium alloy comprised of 6 wt % aluminum and 4 wt % vanadium with a diameter of 1 to 45 micrometers are first provided and exposed to direct metal laser sintering machine using a scan velocity of 1250 mm/s, a scan spacing of 0.10 mm, a layer thickness of 0.030 mm, and a laser power of 43 W for the inner core of each layer, and a laser power of 170 W for the outer, circumferential core layer of dental material. By using these parameters, in some implementations, an implant fixture is produced where the core of the material is about 74% of the total volume of the implant fixture, the strength of the implant fixture is about 300 MPa, and/or the elastic modulus is about 30 GPa, such that the resulting implant fixture has mechanical properties mimicking that of a bone of a subject, properties which, in turn, allows the implant fixture to have a flexible structure and to be capable of decreasing potential bone resorption complications.

Figure 1A:
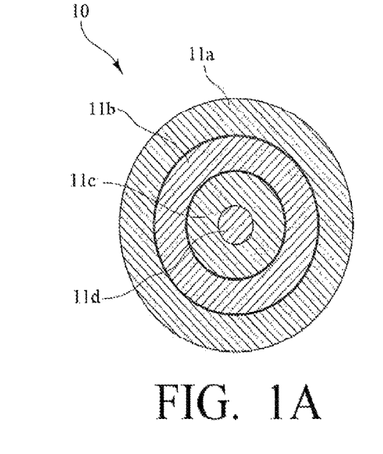
FIGS. 1A-1B are schematic diagrams showing a cross-sectional view (FIG. 1A) and a sagittal view (FIG. 1B) of an exemplary dental prosthesis in the form of a dental implant and fabricated according to the methods of the present invention.
Figure 1B:
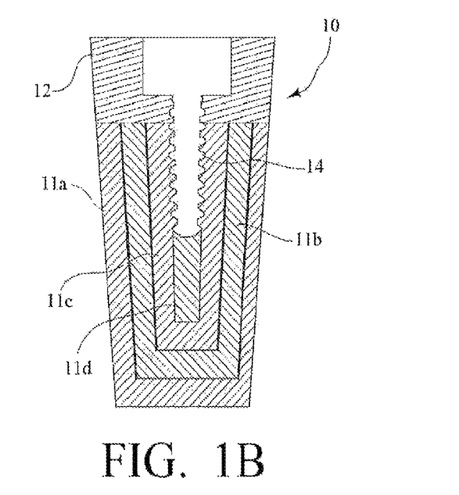

Referring now to FIGS. 1A and 1B, in some implementations of the present invention, a dental implant 10 is produced having multiple layers 11a, 11b, 11c, 11d and a top portion 12 that together define a threaded cavity 14 for securing an implant abutment (not shown). In the implant 10, the multiple layers 11a, 11b, 11c, 11d and the top portion 12 are fabricated to have functionally graded properties that allow the overall properties of the implant 10 to be customized in a manner that not only simulates the surrounding soft and hard tissue, but that also improves the integration of the implant 10 with the surrounding tissue. In this regard, the outer layer 11a of the implant 10 can be fabricated to include a dense or porous structure, with a dense outer layer being used in subjects having dense bones and a porous outer layer being used in subjects having bones with a more porous structure and who may require additional bone contact surface to facilitate bone integration with the surface of the implant 10.

In the implant 10, the top portion 12 is fabricated by more fully melting the dental powder to provide a denser material in the top portion 12 that increases the strength of the implant 10 at the area of the implant that is in contact with the cortical bone of a subject upon its placement and that is commonly subjected to an increased amount of force during both the placement of the implant 10 and the subsequent use of the implant 10 by the subject. In this regard, the top portion 12 is typically fabricated to have a height of up to about 5 mm as such a height typically corresponds to the height of a cortical bone found in the mouth of a subject. However, it is, of course, contemplated that an exemplary implant can be fabricated in accordance with the above-described methods to include a top portion having a height that corresponds to the height of a cortical bone in a particular subject. Additionally, although only four layers 11a, 11b, 11c, and 11d are included in the implant 10 shown in FIGS. 1A-1B, it is contemplated that, depending on the particle size of the dental powder utilized, any number of layers can be included in an exemplary implant of the present invention to produce a desired functionally graded structure.

Figure 2:
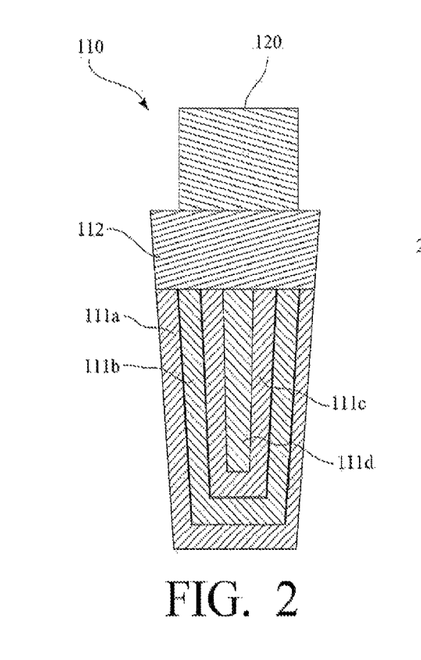
FIG. 2 is a schematic diagram showing a sagittal view of another exemplary dental prosthesis in the form of a dental implant and fabricated according to the methods of the present invention.
Figure 3:
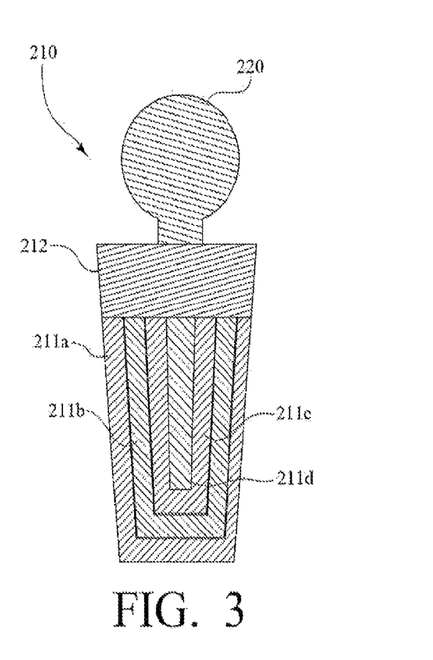
FIG. 3 is a schematic diagram showing a sagittal view of yet another exemplary dental prosthesis in the form of a dental implant and fabricated according to the methods of the present invention.

As another example of a dental implant that can be produced in accordance with the presently-disclosed methods, in some implementations, and referring now to FIG. 2, a dental implant 110 fabricated in accordance with the above-described methods is provided that, similar to the dental implant of FIGS. 1A and 1B, includes multiple functionally graded layers 111a, 111b, 111c, 111d and a top portion 112, with the top portion 112 having a greater density. Unlike the implant 10 shown in FIGS. 1A and 1B, however, the implant 110 does not define a cavity for receiving an implant abutment, but instead includes a square-shaped abutment 120 that is fabricated along with the remainder of the implant 110 to provide an implant having a single unitary structure. Of course, the abutment included on an exemplary implant fabricated in accordance with the presently-disclosed methods can also be fabricated in a variety of additional shapes as well without departing from the spirit and scope of the subject matter described herein. For example, as shown in FIG. 3, an exemplary implant 210 can be provided that, like the implants 10, 110 shown in FIGS. 1A, 1B, and 2, includes multiple functionally graded layers 211a, 211b, 211c, 211d and a top portion 212, but also includes a spherical-shaped abutment 220.

With further respect to the fabrication of a dental implant, in some exemplary implementations, the foregoing methods of fabricating an implant fixture are further varied so as to produce an implant fixture having flexibility at a bottom portion of the fixture (i.e., where the implant fixture contacts the cancellous bone of a subject), but less flexibility at an upper portion of the fixture (i.e., where the implant fixture contacts the cortical bone of a subject and/or is subsequently connected to an implant abutment or a restoration, such as a crown). In these implementations, the foregoing parameters are first utilized to produce the bottom layers of the implant fixture. However, as the height of the implant fixture approaches a height where the implant fixture will attach to an implant abutment or restoration, the parameters are varied so as to produce an implant fixture or portion thereof having a greater strength. For example, in some implementations, a scan velocity of 1250 mm/s, a scan spacing of 0.10 mm, a powder thickness of 0.030 mm and a laser power of 170 W can be used to produce an implant fixture or portion thereof having a density and other mechanical properties that are comparable to currently available implants and/or are capable of withstanding the pressures of normal oral functions. In some implementations, the strength of such resulting implant fixtures is about 300 MPa and the elastic modulus is about 30 GPa. Of course, depending on the particular subject and the particular application, dental implant fixtures having other mechanical properties, such as greater densities, can be produced by adjusting the foregoing parameters or the fraction volume and arrangements of the porous core portions that are found in the implant fixture.

In another exemplary implementation of the present invention, a method of fabricating a dental prosthesis is provided that can be used to produce a dental restoration, such as a replacement crown, where the dental restoration has an outer portion that has mechanical properties (e.g., modulus of elasticity) identical or similar to those of naturally-occurring tooth enamel, and an inner portion that has mechanical properties identical or similar to those of naturally-occurring tooth dentin. For example, in some implementations, the parameters of the process used to selectively melt the dental powders are varied so as to produce an outer, enamel-like portion having an elastic modulus of about 60 to about 120 GPa, a hardness of about 1 to about 4 GPa, and a flexural strength of about 0.6 to about 1.0 GPa; and a core, dentin-like portion having an elastic modulus of about 15 to about 30 GPa, a hardness of about 0.6 to about 1.0 GPa, and a flexural strength of about 0.2 to about 0.6 GPa. In some implementations, the outer, enamel-like portion and the core, dentin-like portion can be manufactured simultaneously while, in other implementations, the two portions can be manufactured independently and then fused together. Furthermore, in some implementations, by knowing the degree of translucency and/or color of the dentin and enamel of a particular subject, a color can be incorporated into the dental restoration during the fabrication process by adding a desired amount of color modifiers and/or by controlling the translucency in each layer. As such, in some implementations, a custom dental restoration can be produced that not only has mechanical properties that mimic those found in the anatomical structures of a natural human tooth, but that also has a color and translucency that mimics those found in the teeth of a particular subject.

Figure 4:
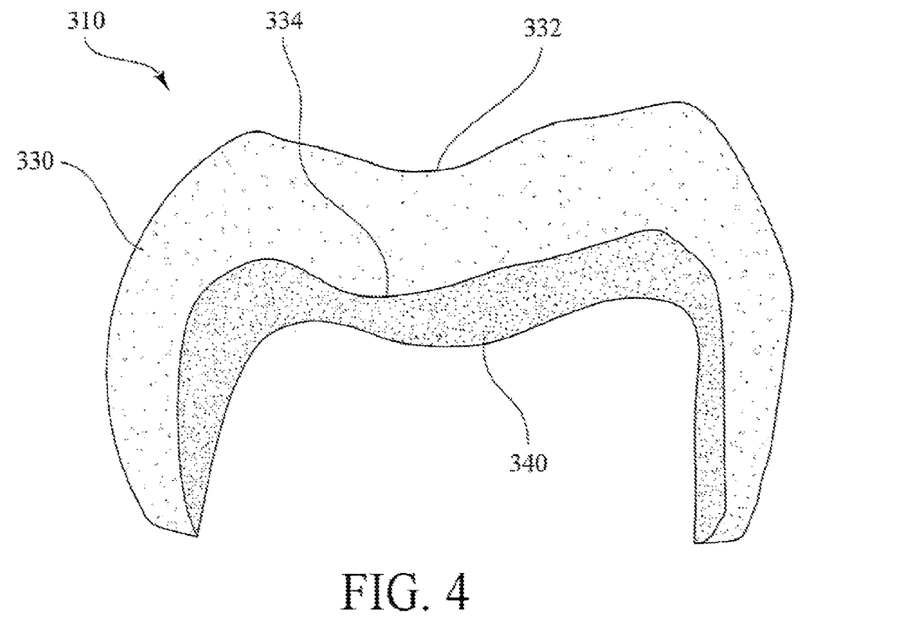
FIG. 4 is a schematic diagram showing a cross-sectional view of an exemplary dental prosthesis in the form of a full contour crown and fabricated according to the methods of the present invention.

Referring now to FIG. 4, as one example of a dental restoration that can be fabricated in accordance with the presently-disclosed methods, a full contour crown 310 can be fabricated that includes an outer enamel-like portion 330 having an outer layer 332 and an inner layer 334, and an inner dentin-like portion 340. Specifically, the full contour crown 310 can be fabricated such that the outer enamel-like portion 330 has a width that extends from the outer layer 332 to the inner layer 334 and that has a hardness and an elastic modulus that reduces across the width of the enamel-like portion from the outer layer 332 to the inner layer 334 to not only produce a functionally graded prosthesis, but to also produce a crown 310 having mechanical properties that correspond to those found in a natural tooth. In some implementations, the crown 310 can be fabricated by selectively melting a dental material to produce an outer layer 332 of the enamel-like portion 330 having an elastic modulus of about 100 GPa to about 140 GPa and a hardness of about 0.8 GPa to about 1.2 GPa, an inner layer 334 of the enamel like-portion 330 having an elastic modulus of about 40 GPa to about 60 GPa and a hardness of about 0.4 GPa to about 0.8 GPa, and a dentin-like portion 340 having an elastic modulus of about 15 GPa to about 45 GPa.

With further regard to the fabrication of a custom dental prosthesis, in some implementations of the methods of the present invention, a method of fabricating a dental prosthesis is provided in which information is first received that relates to a dental or anatomical structure of a subject. Then, a powder of dental implant material is selectively melted based on the information that was received regarding the dental or anatomical structure to thereby produce a three-dimensional dental implant that is specific (e.g., customized) to the dental or anatomical structure in that particular subject. For example, in some implementations, a cone computerized tomography (CT) scan can be used to provide specific information about the quality and quantity of existing dental or anatomical structures, such as bone density, adjacent teeth, blood vessels, sinuses, and nerves. Based on the information obtained from that CT scan, the appropriate size of prosthesis can then be determined within the limitation of the existing dental or anatomical structures, and the existing dental or anatomical structures can be used, for example, to dictate the selection of the width and length of dental prosthesis and, subsequently, the parameters that are utilized to selectively melt a dental powder and then fabricate a dental prosthesis that is customized to the specific subject. In some implementations of the present invention, the information relating to the dental or anatomical structure of a subject can be provided in the form of a digital STL (STereoLithography) file that can then be utilized to fabricate a dental prosthesis (e.g., a crown) having a contour and shape identical or similar to that found in an existing tooth of a subject.

As used herein, the term "subject" includes both human and animal subjects. Thus, veterinary therapeutic uses are provided in accordance with the presently disclosed subject matter.

The present invention is further illustrated by the following specific but non-limiting examples.

EXAMPLES

To evaluate the use of additive manufacturing technology to fabricate functional graded dental prostheses, mechanical test specimens of Ti-6Al-4V were created using a Direct Metal Laser Sintering (DMLS) machine (M270, EOS GmbH, Munich, Germany). The titanium alloy was nominally composed of 6 wt % aluminum, 4 wt % vanadium. The titanium powders were obtained from two vendors, EOS GmbH and Raymor Industries (Quebec, Canada). Both powders had a particle size and geometry that were optimized for use in the DMLS process and that consisted of spherical particles in the 0-45 µm range. The DMLS process, also known as Selective Laser Melting (SLM), used a 200 watt solid-state scanning laser to selectively melt areas of a thin layer of metal powder. Repeated spreading and selective melting of powder layers yielded a three-dimensional metal shape. Depending on the laser energy utilized, the powder was either fully melted—yielding dense material similar to cast metal—or was partially melted—yielding a porous material consisting of metal particles that have sintered together to some degree. The applied laser energy depended on the laser power, scanning velocity, spacing between scan lines and powder layer thickness. In this regard, for purposes of the experiment, the specimens were fabricated using scan velocity 1250 mm/s, a scan spacing of 0.10 mm, and a layer thickness 0.030 mm. Laser power was varied to achieve full (170 W) or partial (43 W or 85 W) melting.

Figure 5A:
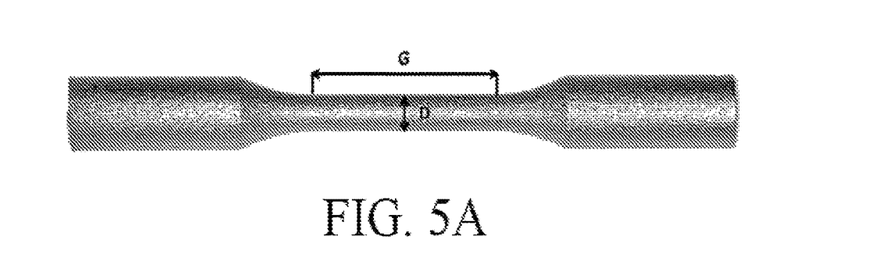
FIGS. 5A-5B are images of test specimens fabricated according to the methods of the present invention, including an image showing a specimen having a reduced section diameter (D) of 5.0 mm and a gage length (G) of 25 mm (FIG. 5A) and an image showing the completed specimens prior to separating the specimens from the support structure (FIG. 5B)
Figure 5B:
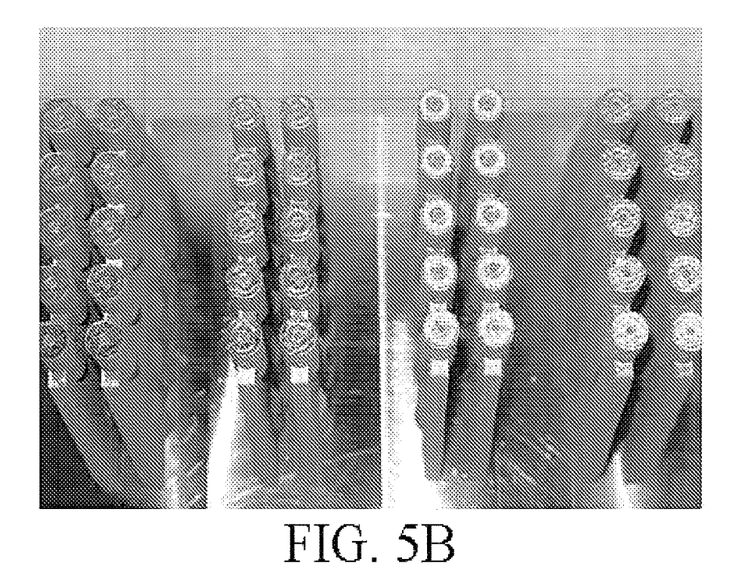

During the DMLS process, cylindrical tensile test specimens were built in a vertical orientation with a "skin-core" structure to reflect a prototype implant design. The geometry of the specimen conformed to the standard for tensile testing of metals (ASTM test method E8M, ASTM International, West Conshohocken, Pa.) and had a reduced section diameter of 5.0 mm and a gage length of 25 mm (FIGS. 5A and 5B). The fully dense, outer "skin" of each specimen was scanned at the highest laser power. The outer skin thickness was set at 0.35, 1.00 and 1.50 mm for different specimens. The specimens' specifications are shown in Table 1 below. The inner "core" region of each specimen was scanned at one of the lower laser powers. One set of specimens was fabricated at fully density as the control group, i.e. the skin dimension was set to greater than 2.5 mm, yielding fully melted, dense material throughout. All specimens were subjected to a stress-relieving heat treatment of 625° C. for 2.5 hours in argon.

TABLE 1

Specifications of Test Groups and Mechanical Properties of Fabricated Structures.

| Laser (W) | skin (mm) | Yield Stress (MPa) | s.d. | Fracture Stress (MPa) | s.d. | Elastic Modulus (GPa) | s.d. | N |
|---|---|---|---|---|---|---|---|---|
| 170 | — | 1080 | 41 | 1118 | 16 | 104 | 3 | 10 |
| 85 | 1.50 | 1011 | 19 | 1035 | 18 | 103 | 2 | 10 |
| 85 | 1.00 | 886 | 18 | 898 | 18 | 91 | 2 | 10 |
| 85 | 0.35 | 631 | 59 | 658 | 42 | 83 | 1 | 10 |
| 43 | 1.50 | 928 | 9 | 965 | 9 | 95 | 1 | 10 |
| 43 | 0.35 | 286 | 57 | 286 | 39 | 35 | 6 | 10 |

Subsequent to fabrication, specimens were then tested in tension using an Instron 5569A 50 kN test machine (Norwood, Mass.) under displacement control at 2.5 mm/min. Tensile modulus, yield stress and stress-at-fracture were determined from load cell and strain gage output using Instron's Bluehill software. Ten replicate tests were performed for each set of build parameters. After testing, a cross-section from one specimen of each set was mounted, polished and examined in reflected light using a Olympus MX 5 optical microscope.

The observed mechanical properties of the specimens are shown in Table 1 above. Tensile modulus, yield stress, and stress-at-fracture for skin-core specimens were all lower than that of the fully dense material. As expected, the strength and stiffness of the material decreased as skin thickness and laser power decreased. All measurements showed good reproducibility with standard deviations generally less than 2% of the measured value. The only exceptions were the two sets of specimens with the smallest skin thicknesses. For these, the variability of the strength measurements was significantly greater than that of the denser specimens. For both of those sets, the core comprised 74% of the specimen volume. In this regard, while it was not possible to identify crack origins from fracture surface micrographs of those specimens, it was thought that the fracture initiated in the porous core. The observed large variability in the strength measurements was also consistent with the irregular nature of the core porosity and the range of pore sizes observed (see, e.g., FIGS. 6C and 7B).

Figure 6A:
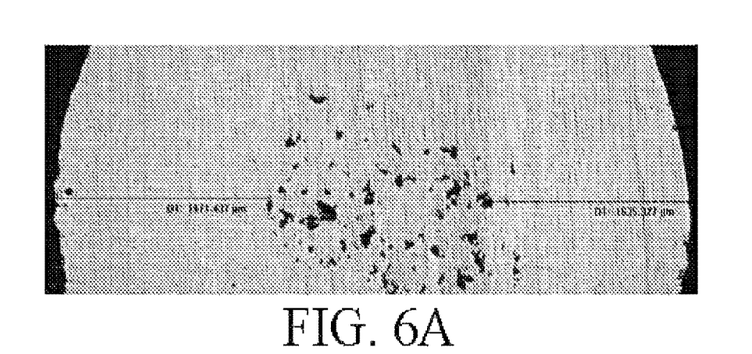
FIGS. 6A-6C are images showing optical micrographs of three specimens having a partially sintered core structure produced with an 85 W laser and having various skin or outer layer thicknesses, including an image of a specimen having a 1.5 mm thick skin (FIG. 6A), an image of a specimen having a 1.0 mm thick skin (FIG. 6B), and an image of a specimen having a 0.35 mm thick skin (FIG. 6C)
Figure 6B:
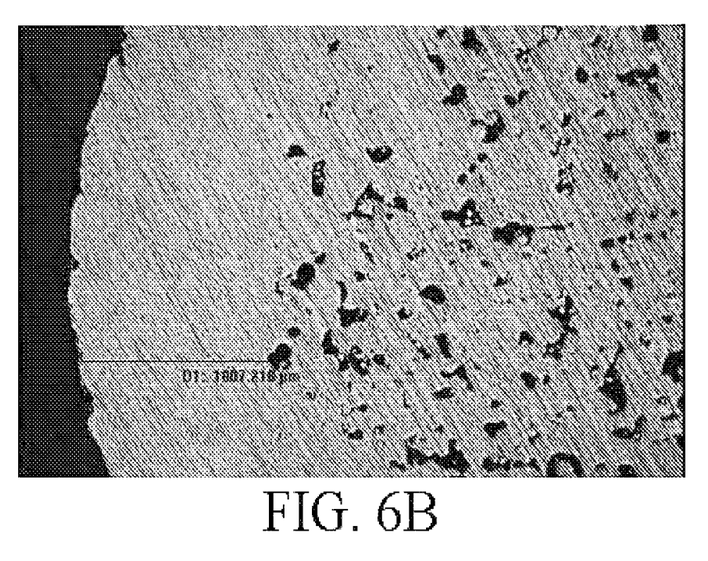
Figure 6C:
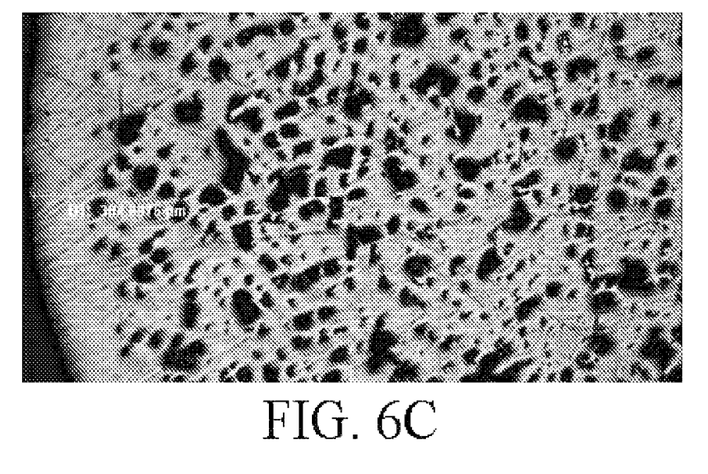
Figure 7A:
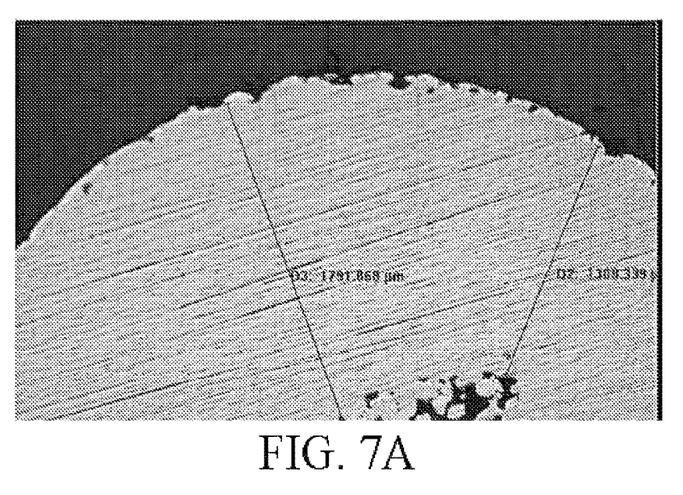
FIGS. 7A-7B are images showing optical micrographs of two specimens having a partially sintered core structure produced with a 43 W laser, including an image of a specimen having a 1.5 mm thick skin (FIG. 7A) and an image of a specimen having a 0.35 mm thick skin (FIG. 7B)
Figure 7B:
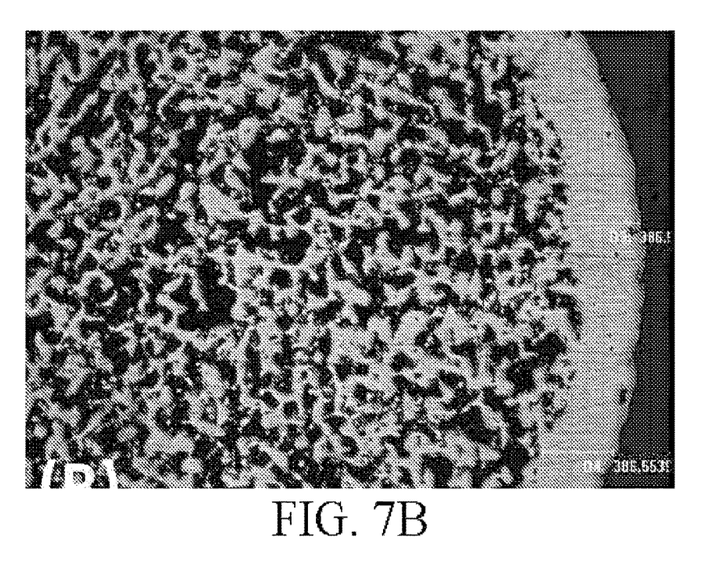

FIGS. 6A, 6B, and 6C show optical micrographs of three specimens having partially sintered core structure produced with 85 W laser powers and having a skin thicknesses of 1.5 mm, 1.0 mm and 0.35 mm respectively. FIGS. 7A and 7B show optical micrographs of three specimens having partially melted core structures produced with 43 W laser powers and having skin thicknesses of 1.5 mm and 0.35 mm, respectively. The partially sintered core was clearly visible in all specimens, with somewhat greater porosity for the lower laser power specimens. The thickness of skin was close to the nominal value, although there was no distinct boundary between the dense skin and the irregular, porous core.

It has been proposed that the placement of custom-made root-analogue implants into the extraction socket can be used to reduce bone and soft-tissue trauma. [24]. The initial clinical studies with root-identical titanium implant demonstrated favorable results with 100% primary stability at insertion and 1-month follow up. However, an extremely high failure rate of 48% was found over a short time period of 9 months post operation. [25, 26] In a more recent clinical trial, immediate, non-submerged, custom-made root-analogue zirconia implants (with surface macro-retentive feature and reduced implant diameter at the cortical bone area) were placed into single-rooted extraction sockets and showed an overall survival rate of 92% up to 33 months under functions. [27] Satisfactory esthetic and functional results were achieved with the composite crown in that study with minimal soft and hard peri-implant tissue resorption.

In contrast to the previous studies, the design of the titanium specimens described above simulated a new design concept for implants. The dense outer layer provided sufficient surface hardness and strength to withstand an insertion procedure, and the partially-sintered inner layer with various volume and porosity distribution allowed for control over the desired overall stiffness of implant. In conjunction with the selective laser sintering process, it was thus feasible to fabricate a custom implant from a three-dimensional virtual file that would exhibit a desired geometry and desired functionally graded mechanical properties. In this regard, the foregoing study was further focused on finding the effect of various fabrication parameters (different laser energy, solid skin thickness) on the selected mechanical properties (fracture stress, and elastic modulus) of resulting specimens.

As shown in Table 1, the gradient structure of titanium specimens that were fabricated with a 43 W laser to produce a sintered porous core and that had a solid skin thickness of 0.35 mm demonstrated a Young's modulus of 35 GPa and a fracture stress of 286 MPa. Although the resulted Young's modulus was similar to that of bone, the fracture strength was roughly 25% of the strength of full density specimens. It was found that the reduced Young's modulus was accompanied by reduced fracture stress. Previous finite element analysis (FEA) studies have suggested that the maximum stress of dental implants under loading was observed at implant the neck, cortical bone areas. [28,29] Although the implant diameter, length, placement depth, and loading angle can affect the stress distribution of osseointegrated implants, the fabrication parameters identified in the above-described research that yielded a reduced Young's modulus and strength were thought to be more suitable to fabricate the apical-half of the implant fixture where the lower stress occurs. One benefit of additive manufacturing process is that custom-made implants with user-defined complexity can be fabricated, and several fabrication parameters can be combined in one individual implant fixture. Based on the findings of FEA studies, the implant neck areas may be more suitable to be produced with fully melted, dense material.

The pore structure shown in FIGS. 6A-6C and FIGS. 7A-7B consisted of discrete, isolated pores surrounded by dense, fully connected solid material. The dense regions of the structure were significantly coarser than the 45 μm maximum particle size, suggesting good melting and bonding of the powder particles at both laser powers. Comparing the specimens with same skin thickness, the amount of porosity was higher when the lower laser power was used to produce the partially sintered core structure. (FIG. 6A vs. FIG. 7A; FIG. 6C vs. FIG. 7B). However, the amount of porosity in the core region was not related to the laser power alone. The laser energy applied to form the dense skin influences the temperature and the sintering in the core region. Comparing FIG. 6C to FIGS. 6A and 6B, a relatively thin skin leads to higher porosity for the same laser power values on the core structure (85 W). FIGS. 7A-7B demonstrate a similar effect in that a thinner skin layer leads to higher porosity for the same power values on the core structure (43 W).

Figure 8A:
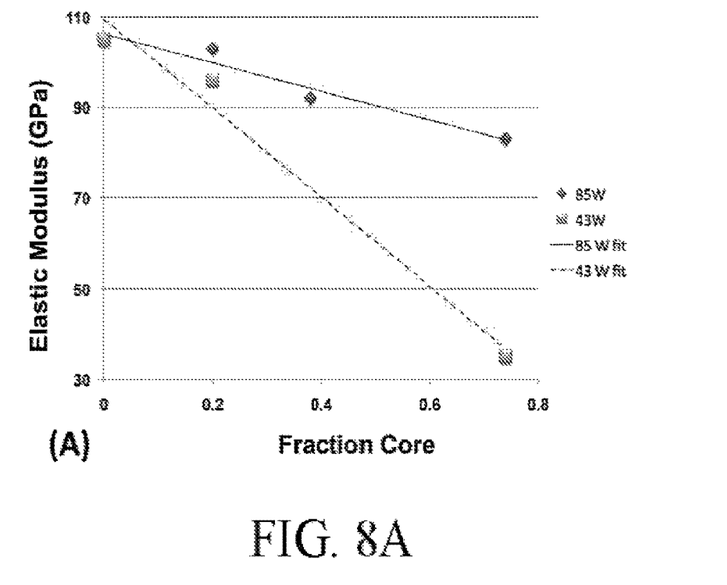
FIGS. 8A-8B are graphs showing the elastic modulus of exemplary dental implants produced according to the methods of the present invention, both as a function of fraction core (FIG. 8A) and fracture stress (FIG. 8B).

As noted, the measured elastic modulus depends on both the laser power and the skin thickness. In this regard, the composite modulus could be modeled using a "rule-of-mixtures" approach, assuming that the modulus of the partial dense core was less than that of the dense skin. FIG. 8A shows the elastic modulus as a function of the fraction core (total volume percentage of porous core structure), which was calculated from the nominal skin thickness and the specimen diameter. The lines show calculated values assuming core material moduli of 73 and 16 GPa for the 85 W and 43 W laser powers, respectively. The lowest modulus achieved, 35 GPa, was similar to that of bone. That value was achieved for a laser power of 43 W and a skin thickness of 0.35 mm, producing a core that is 74% of the total volume. Based on the "rule-of-mixtures" model, other combinations of laser power and skin thickness could achieve that same modulus value. In comparing these values with previous studies, others have selected different fabrication parameters with a direct laser metal sintering technique using a continuous 200 W of laser energy and alloy powder (Ti-6Al-4V) with a particle size of 1-10 μm, with the resulting Young's modulus of the inner core material (defined as compact titanium group) being 104±7.7 GPa, and that of the outer porous material (defined as porous titanium group) being 77±3.5 GPa. In the foregoing experiments, however, the gradient structure of the titanium specimens produced with a 43 W laser sintered porous core (a core that is 74% of the total volume) and a solid skin thickness of 0.35 mm, further reduced the Young's modulus to 35 GPa which is more similar to observed in bone.

Figure 8B:
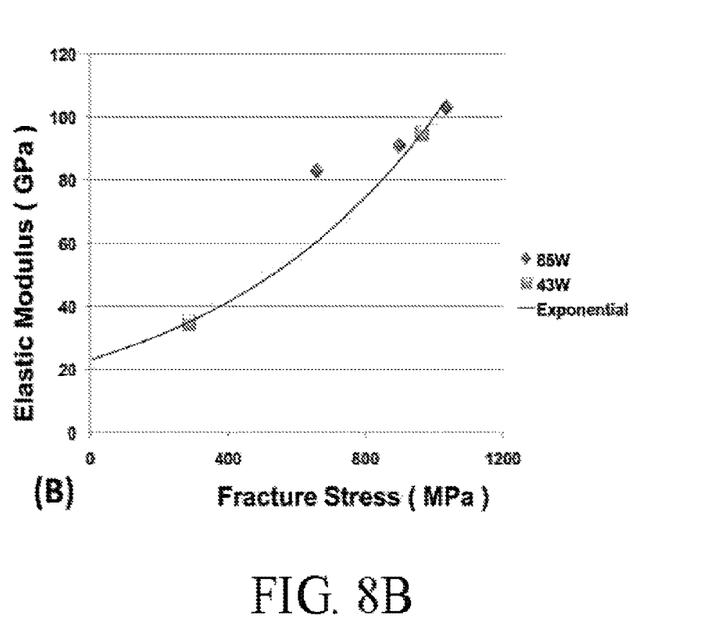

The fracture stress of the skin-core composite produced in the presently-described study also decreased as the laser power and skin thickness decreased. FIG. 8B shows the relationship between elastic modulus and fracture stress for all of the specimens. While not strictly linear, it appeared that achieving a modulus less that 20 GPa was difficult with a simple skin-core structure, as below that value, the fracture stress would be zero. The calculated stress for these tests was based on the total force and cross-sectional area of the specimens. As these were composite structures consisting of materials with different moduli, the local stress at any point within the specimen varied from the average value. A simple rule-of-mixture calculation showed that the maximum stress in the dense skin was much lower than that measured for the full density titanium specimen. This supported the thought that the fracture origin for the composite specimens was within the core region.

The foregoing study thus provided a set of fabrication parameters for the production of functionally graded titanium dental implants. Within the findings of foregoing study, the additive manufacturing technology (Direct Metal Laser Sintering) was observed to produce specimens with defined and well-controlled porosity core structure, fully sintered skin and physical geometry based on a digital STL (Stereolithography) file. The achieved physical geometry and the mechanical properties in the current study demonstrated the proof of concept to have a custom dental implant fabricated with functionally graded structure, which is better adapted to the elastic properties of the bone and the long-term performance of such dental implants may be improved.

Throughout this document, various references are mentioned. All such references are incorporated herein by reference, including the references set forth in the following list:

REFERENCES

1. Kuroda D, Niinomi M, Morinaga M, Kato Y, Yashiro T. Design and mechanical properties of new b type titanium alloys for implant materials. Mater Sci Eng A. 1998; 243:244-9.
2. Niinomi M. Mechanical biocompatibilities of titanium alloys for biomedical applications. J Mech Behav Biomed Mater. 2008; 1:30-42.
3. Guillemot F. Recent advances in the design of titanium alloys for orthopedic applications. Expert Rev Med Devices. 2005; 2:741-8.
4. Parr G. Titanium: the mystery metal of implant dentistry. J Prosthet Dent. 1985; 54:410-3.
5. Bhattarai S R, Khalil K A, Dewidar M, Hwang P H, Yi H K, Kim H Y. Novel production method and in-vitro cell compatibility of porous Ti-6Al-4V alloy disk for hard tissue engineering. J Biomed Mater Res A. 2008; 86:289-99.
6. Krishna B V, Bose S, Bandyopadhyay A. Low stiffness porous Ti structures for load-bearing implants. Acta Biomater. 2007; 3:997-1006.
7. Turner T M, Sumner D R, Urban R M, Rivero D P, Galante J O. A comparative study of porous coatings in a weight-bearing total hip-arthroplasty model. J Bone Joint Surg Am. 1986; 68:1396-409.
8. Head W C, Bauk D J, Emerson Jr R H. Titanium as the material of choice for cementless femoral components in total hip arthroplasty. Clin Orthop Relat Res. 1995; 311: 85-90.
9. Oh I H, Nomura N, Masahashi N, Hanada S. Mechanical properties of porous titanium compacts prepared by powder sintering. Scripta Mater. 2003; 49:1197-202.
10. Hollander D A, von Walter M, Wirtz T, Sellei R. Structural, mechanical and in vitro characterization of individually structured Ti-6Al-4V produced by direct laser forming. Biomaterials. 2006; 27:955-63.
11. Stamp R, Fox P, O'Neill W, Jones E, Sutcliffe C. The development of a scanning strategy for the manufacture of porous biomaterials by selective laser melting. J Mater Sci Mater Med. 2009; 20:1839-48.
12. Deckard C, Beaman J J. Process and control issues in selective laser sintering. ASME Prod Eng Div (Publication) PED 1988; 33:191-7.
13. Traini T, Mangano C, Sammons R L, Mangano F Direct laser metal sintering as a new approach to fabrication of an isoelastic functionally graded material for manufacture of porous titanium dental implants. Dent Mater. 2008; 24:1525-33.
14. Mullen L, Stamp R C, Brooks W K, Jones E, Sutcliffe C J. Selective Laser Melting: a regular unit cell approach for the manufacture of porous, titanium, bone in-growth constructs, suitable for orthopedic applications. J Biomed Mater Res B Appl Biomater. 2009; 89:325-34.
15. Santos E C, Shiomi M, Osakada K, Laoui T. Rapid manufacturing of metal components by laser forming. Int J Mach Tools Manuf. 2006; 46:1459-68.
16. Lu L, Fuh J, Wong Y. Laser-Induced Materials and Processes for Rapid Prototyping. Norwell, Mass.: Kluwer Academic Publishers; 2001.
17. Tolochko N K, Laoui T, Khlopkov Y V, Mozzharov S E, Titov V I, Ignatiev M B. Absorptance of powder materials suitable for laser sintering. Rapid Prototyping J. 2000; 6:155-160.
18. Bandyopadhyay A, Espana F, Balla V K, Bose S. Influence of porosity on mechanical properties and in vivo response of Ti6Al4V implants. Acta Biomater. 2010; 6:1640-8.
19. Pillar R M. Porous-surfaced metallic implants for orthopaedic applications. J Biomed Mater Res—Appl Biomater. 1987; 21:1-33.
20. Clemow A J T, Weinstein A M, Klawitter J J, Koeneman J, Anderson J. Interface mechanics of porous titanium implants. J Biomed Mater Res. 1981; 15:73-82.
21. Wennerberg A, Albrektsson T. Effects of titanium surface topography on bone integration: a systematic review. Clin Oral Implants Res. 2009; 20:172-84.
22. Shalabi M M, Gortemaker A, Van't Hof M A, Jansen J A, Creugers N H. Implant surface roughness and bone healing: a systematic review. J Dent Res. 2006; 85:496-500.
23. Le Guéhennec L, Soueidan A, Layrolle P, Amouriq Y. Surface treatments of titanium dental implants for rapid osseointegration. Dent Mater. 2007; 23:844-54.
24. Hodosh M, Povar M, Shklar G. The dental polymer implant concept. J Prosthet Dent. 1969:22: 371-80.
25. Pirker W, Kocher A Immediate, non-submerged, root-analogue zirconia implant in single tooth replacement. Int J Oral Maxillofac Surg. 2008; 37:293-5.
26. Kohal R J, Hürzeler M B, Mota L F, Klaus G, Caffesse R G, Strub J R. Custom-made root analogue titanium implants placed into extraction sockets. Clin Oral Implants Res. 1997:8:386-392.
27. Pirker W, Kocher A Immediate, non-submerged, root-analogue zirconia implants placed into single-rooted extraction sockets: 2-year follow-up of a clinical study. Int J Oral Maxillofac Surg. 2009; 38:1127-32.
28. Baggi L, Cappelloni I, Di Girolamo M, Maceri F, Vairo G. The influence of implant diameter and length on stress distribution of osseointegrated implants related to crestal bone geometry: a three-dimensional finite element analysis. J Prosthet Dent. 2008; 100:422-31.
29. Lee J S, Cho I H, Kim Y S, Heo S J, Kwon H B, Lim Y J. Bone-implant interface with simulated insertion stress around an immediately loaded dental implant in the anterior maxilla: a three-dimensional finite element analysis. Int J Oral Maxillofac Implants. 2012; 27:295-302.
30. Van Noort R. The Future of Dental Devices is Digital. Dental Materials. 2012; 28:3-12.
31. Zhang Y, Chai H, Lawn B R. Graded Structures for All-Ceramic Restorations. J Dent Res. 2010; 89(4):417-421.
32. Atzeni E, Iuliano L, Minetola P, Salmi A. Proposal of an Innovative Benchmark for Accuracy Evaluation of Dental Crown Manufacturing. Computers in Biology and Medicine. 2012; 42:548-555.
33. He L H, Yin Z H, Van Vuuren U, Carter E A, Liang X W. A Natural Functionally Graded Biocomposite Coating—Human Enamel. Acta Biomaterialia. 2012.
34. Silva N F R A, Witek L, Coelho P G, Thompson V P, Rekow, E D, Smay J. Additive CAD/CAM Process for Dental Prostheses. Journal of Prosthodontics. 2011; 20:93-96.
35. Ebert J, Ozkol E, Zeichner A. Uibel K, Weiss O, Koops U, Telle R, Fischer H. Direct Inkject Printing of Dental Prostheses Made of Zirconia. Journal of Dental Research. 2009; 88(7):673-676.
36. Anusavice K J. Dental Ceramics. Phillips, Science of Dental Materials. 12$^{th}$ edn. Sounders, 2003:655-719.
37. Conrad H J, Seong W J, Pesun I J. Current ceramic materials and systems with clinical recommendations. J Prosthet Dent, 2007; 98:389-404.
38. Giannakopoulos A E, et al. Development of strong surfaces using functionally graded composites inspired by natural teeth. Journal of engineering materials and technology, 2010 132(1).
39. Li H H, et al. A natural functionally graded biocomposite coating-human enamel. Acta Biomaterialia. Epub ahead of print.
40. U.S. Patent Application Publication No. 2008/0213727
41. U.S. Pat. No. 7,666,522.
42. U.S. Pat. No. 7,951,412.
43. U.S. Pat. No. 8,491,936.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A method of fabricating a dental prosthesis, comprising the steps of:
   (a) providing a powder of a dental material;
   (b) selectively melting the powder of the dental material to produce a functionally graded layer of the dental material; and
   (c) repeating steps (a) and (b) to produce a three-dimensional dental prosthesis having a functionally graded structure,
   wherein the three-dimensional dental prosthesis is a full contour crown, the full contour crown including an outer enamel-like portion having an outer layer and an inner layer, and the full contour crown including an inner dentin-like portion,
   wherein the outer enamel-like portion has a width extending from the outer layer to the inner layer, and wherein a hardness and an elastic modulus of the enamel-like portion reduces across the width of the enamel-like portion from the outer layer to the inner layer, and
   wherein the outer layer of the enamel-like portion has an elastic modulus of about 100 GPa to about 140 GPa and a hardness of about 0.8 GPa to about 1.2 GPa, and wherein the inner layer of the enamel like-portion has an elastic modulus of about 40 GPa to about 60 GPa and a hardness of about 0.4 GPa to about 0.8 GPa.

2. The method of claim 1, wherein selectively melting the powder of the dental material comprises selective laser melting of the powder of the dental material.

3. The method of claim 1, wherein the dental material is selected from the group consisting of a metal, a metal alloy, a ceramic, a resin material, and combinations thereof.

4. The method of claim 3, wherein the ceramic is selected from the group consisting of lithium disilicate, leucite, and mica, wherein the metal is selected from titanium and gold, and wherein the metal alloy is selected from titanium alloy and gold alloy.

5. The method of claim 4, wherein the dental material comprises a titanium alloy having about 6 wt % aluminum and about 4 wt % vanadium.

6. The method of claim 1, wherein the dentin-like portion has an elastic modulus of about 15 GPa to about 45 GPa.

* * * * *